(12) United States Patent
Huetter et al.

(10) Patent No.: US 7,588,367 B2
(45) Date of Patent: Sep. 15, 2009

(54) THERMOANALYTICAL SENSOR

(75) Inventors: Thomas Huetter, Niederrohrdorf (CH); Melchior Zumbach, Lenzburg (CH)

(73) Assignee: Mettler-Toledo AG, Greifensee (CH)

( * ) Notice: Subject to any disclaimer, the term of this patent is extended or adjusted under 35 U.S.C. 154(b) by 0 days.

(21) Appl. No.: 11/976,332

(22) Filed: Oct. 23, 2007

(65) Prior Publication Data

US 2008/0080586 A1    Apr. 3, 2008

Related U.S. Application Data

(63) Continuation of application No. PCT/EP2006/061746, filed on Apr. 21, 2006.

(30) Foreign Application Priority Data

Apr. 25, 2005  (EP)  ................................. 05103341

(51) Int. Cl.
*G01K 17/00* (2006.01)
*G01K 7/02* (2006.01)
*G01K 13/10* (2006.01)

(52) U.S. Cl. ............................ 374/31; 374/10; 374/29; 374/179

(58) Field of Classification Search ............. 374/10–12, 374/29–40, 179, 185, 135, 137, 43–44, 100, 374/163, 208; 73/24.04, 29.01, 23.2, 23.25, 73/23.4, 25.03, 25.01, 75; 436/147; 422/51
See application file for complete search history.

(56) References Cited

U.S. PATENT DOCUMENTS

| 3,339,002 | A | * | 8/1967 | Pelanne | 264/255 |
| 3,382,714 | A | * | 5/1968 | Miller et al. | 374/29 |
| 3,801,949 | A | * | 4/1974 | Larrabee | 338/22 R |
| 4,007,435 | A | * | 2/1977 | Tien | 338/34 |
| 4,507,643 | A | * | 3/1985 | Sunano et al. | 338/34 |
| 4,577,976 | A | * | 3/1986 | Hayashi et al. | 374/29 |
| 4,738,706 | A | * | 4/1988 | Picinelli | 65/29.21 |
| 5,033,866 | A | * | 7/1991 | Kehl et al. | 374/179 |
| 5,121,993 | A | * | 6/1992 | Carrigan et al. | 374/29 |

(Continued)

FOREIGN PATENT DOCUMENTS

DE    3237912 A  *  4/1984

(Continued)

OTHER PUBLICATIONS

Franz X. Eder, "Arbeitsmethoden der Thermodynamik", New York 1983, p. 240.

(Continued)

*Primary Examiner*—Gail Verbitsky
(74) *Attorney, Agent, or Firm*—Buchanan Ingersoll & Rooney PC

(57) ABSTRACT

Thermoanalytical sensor for calorimetric measurements which cooperates with a temperature control device and comprises at least one measurement position formed on the sensor, a heat flow path established between the temperature control device and the at least one measurement position, and at least one temperature-measuring element, characterized in that the sensor has a plurality of layers which are formed substantially by ceramic elements that have been solidly bonded to each other by undergoing a sintering process together and which in their green state can be provided with a structure, wherein at least a part of the ceramic elements are structured.

16 Claims, 3 Drawing Sheets

U.S. PATENT DOCUMENTS

| | | | |
|---|---|---|---|
| 5,334,350 A * | 8/1994 | Friese et al. | 422/98 |
| 5,608,154 A * | 3/1997 | Kato et al. | 73/23.31 |
| 5,813,764 A * | 9/1998 | Visser et al. | 374/12 |
| 5,989,398 A | 11/1999 | Young et al. | |
| 6,036,927 A | 3/2000 | Chatterjee et al. | |
| 6,071,476 A * | 6/2000 | Young et al. | 422/51 |
| 6,202,480 B1 | 3/2001 | Mauze et al. | |
| 6,238,085 B1 * | 5/2001 | Higashi et al. | 374/10 |
| 6,278,051 B1 * | 8/2001 | Peabody | 136/225 |
| 6,318,890 B1 * | 11/2001 | Hutter et al. | 374/10 |
| 6,406,181 B1 * | 6/2002 | Mueller et al. | 374/185 |
| 6,435,005 B1 * | 8/2002 | Kikuchi et al. | 73/25.01 |
| 6,508,585 B2 * | 1/2003 | Nakamura et al. | 374/12 |
| 6,662,121 B1 * | 12/2003 | Oda et al. | 702/45 |
| 6,676,287 B1 * | 1/2004 | Mathis et al. | 374/1 |
| 6,732,567 B2 * | 5/2004 | Briscoe et al. | 73/23.39 |
| 6,773,565 B2 * | 8/2004 | Kunimoto et al. | 204/425 |
| 6,872,879 B1 * | 3/2005 | Serras et al. | 136/205 |
| 6,984,298 B2 * | 1/2006 | Polikarpus et al. | 204/424 |
| 7,083,710 B2 * | 8/2006 | Scheer et al. | 204/427 |
| 7,160,422 B2 * | 1/2007 | Imamura et al. | 204/431 |
| 7,189,360 B1 * | 3/2007 | Ho | 422/82.02 |
| 7,280,028 B2 * | 10/2007 | Nelson et al. | 338/22 R |
| 7,338,640 B2 * | 3/2008 | Murthy et al. | 422/83 |
| 7,473,030 B2 * | 1/2009 | Bruce et al. | 374/31 |
| 2001/0002201 A1 * | 5/2001 | Kita et al. | 374/140 |
| 2002/0023914 A1 * | 2/2002 | Kitagawa et al. | 219/444.1 |
| 2002/0174937 A1 | 11/2002 | Burdon et al. | |
| 2003/0128096 A1 | 7/2003 | Mazzochette | |
| 2003/0152128 A1 * | 8/2003 | Verhaegen | 374/30 |
| 2003/0154764 A1 * | 8/2003 | Stahl et al. | 73/23.2 |
| 2005/0016258 A1 * | 1/2005 | Suzuki et al. | 73/31.05 |
| 2007/0212263 A1 * | 9/2007 | Shin et al. | 422/95 |

FOREIGN PATENT DOCUMENTS

| | | |
|---|---|---|
| DE | 39 16 311 A1 | 10/1990 |
| DE | 103 40 748 A1 | 3/2005 |
| EP | 0 990 893 A1 | 4/2000 |
| JP | 55106347 A * | 8/1980 |
| JP | 58129228 A * | 8/1983 |

OTHER PUBLICATIONS

International Search Report.
European Search Report.

* cited by examiner

THERMOANALYTICAL SENSOR

RELATED APPLICATIONS

This application claims priority under 35 U.S.C. §119 to EP Application 05103341.3 filed in European Patent Office on 25 Apr. 2005, and as a continuation application under 35 U.S.C. §120 to PCT/EP2006/061746 filed as an International Application on 21 Apr. 2006 designating the U.S., the entire contents of which are hereby incorporated by reference in their entireties.

TECHNICAL FIELD

A thermoanalytical sensor for calorimetric measurements is disclosed.

BACKGROUND INFORMATION

Calorimetric measurements serve to determine the amounts of heat turned over in chemical or physical processes as well as the specific heat of a substance. To perform this measurement, the substance or, more specifically, a substance sample, is heated in a calorimeter under controlled conditions, and the heat flow between a substance sample and a temperature control device (i.e. a device for heating and/or cooling) is observed by means of a thermoanalytical sensor. The heat flow is frequently determined by way of the temperature differences along the heat flow path between the sample and the temperature control device.

A calorimeter includes in general at least one measuring chamber with a thermoanalytical sensor on which at least one measurement position is arranged. The sensor is on the one hand thermally coupled to a temperature control device and on the other hand to a sample which is in contact with the sensor and/or to a reference. The temperature control device and/or the sensor is connected through suitable means to at least one controller unit.

Calorimeters can be used for example in the area of thermal analysis for the investigation of the most diverse kinds of substances. In general, a sample of the substance is set on a sample position formed on the sensor and is heated by means of a temperature control device, with the sample being held in most cases inside a special cup which can be closed up. The heat flow which occurs between the temperature control device and the sample is measured and evaluated. This can provide information about the structure and the composition of the substance, such as for example its heat capacity, phase transitions and oxidation stability. It is further possible to observe kinetic reactions and/or to make determinations of purity.

In calorimetric measurements that are to be performed with a high accuracy and over a large temperature range, the general procedure is to measure the heat flow of a sample in relation to the heat flow of a reference. Calorimetric measurements can be performed in calorimeters with separate measurement chambers as well as with a shared measurement chamber for at least one sample and at least one reference.

For accurate measurements with a high reproducibility, it is important that the sensor has a high mechanical, chemical as well as thermal stability. Sensors of the known state of the art often include a disk-shaped carrier with at least one thermocouple arrangement and at least one measurement position formed on the sensor. The thermocouple arrangement as well as the measurement position can be produced for example by means of thin-film technology or thick-film technology.

Sensors with thermocouples produced by thin-film technology that are part of a thermocouple arrangement are described for example in F. X. Eder, Arbeitsmethoden der Thermodynamik (*Work Methods in the Field of Thermodynamics*), Volume 2, Springer-Verlag 1983, page 240. Sensors produced by means of thin-film technology have the disadvantages that the production process is expensive, that the maximum thickness which can be realized is very small, and that they have in many cases a low mechanical and/or chemical endurance.

More resistant sensors can be produced by means of thick-film technology. A sensor on which one sample position and one reference position are formed and which has at least two thermocouple arrangements is disclosed in DE 39 16 311 C2. Sensors produced with thick-film technology can have several thick-film coating layers formed on a carrier substrate. The maximum overall thickness of the coating layers is about 100 μm, with the individual layers having a typical thickness between 5 and 20 μm. The individual coating layers can include electrical circuits such as for example thermocouple arrangements and are separated from each other by insulating layers. The layers are deposited by means of pastes and screen-printing techniques, and normally each printing step has to be followed by a firing process. As a result, the production process in particular for several coating layers is very time-consuming. The many sintering steps can have a detrimental effect on the structure and the properties of the coating materials involved and/or on the carrier substrate.

For the production of thermocouples, at least two different thermo-pastes are deposited on the carrier substrate which consists in most cases of a ceramic material. There can be a voltage difference between two thermocouples that are arranged at a distance from each other, through which a temperature difference can be determined. The thermocouples can be arranged in specific patterns that are prescribed for the deposition of the respective thick-film coatings.

With thin-film technology as well as with thick-film technology it is possible to implement substantially two-dimensional thermocouple arrangements which detect temperature changes within the layer of the sensor that contains thermocouples. The thermocouples are normally disposed in a substantially horizontal layer of the sensor, either on the sensor surface itself or near the latter.

However, the heat flow in the sensor is not confined within a layer but propagates in three dimensions in the entire sensor. Thus, only a part of the heat flow can be measured with a substantially two-dimensional thermocouple arrangement produced with thin- or thick-film technology, so that the result of the measurement carries a corresponding uncertainty.

SUMMARY

A thermoanalytical sensor is disclosed for calorimetric measurements which, in comparison to conventional sensors, offers a higher level of sensitivity and, most of all, a greater structural flexibility.

A thermoanalytical sensor for calorimetric measurements cooperates with a temperature control device and includes at least one measurement position formed on the sensor, and a temperature-measuring element. A heat flow path establishes itself between the measurement position and the temperature control device. The sensor mainly comprises several layers which are formed by ceramic elements that have been solidly bonded to each other by undergoing a sintering process together. The ceramic elements are formed essentially of a ceramic which in its green state can be provided with a structure. At least a part of the ceramic elements that form the sensor are structured.

The term "layer" in this context refers to the position and area occupied by a ceramic element in the sensor after the joint sintering. The term "ceramic element" is used in the following for a ceramic element in the unsintered or green state. The joint sintering produces a solid bond between the ceramic elements, so that a nearly monolithic unit is formed. The term "layer" serves mostly to give a better understanding of the configuration of the sensor.

The individual ceramic elements can be individually structured before the sintering, whereby the shape and the structure of the sensor can be adapted and shaped in almost any way desired. A sensor is normally comprised of structured as well as unstructured ceramic elements. The ceramic elements are sintered together at one time and are therefore all subjected to the same heating profile, whereby the thermal stress on individual ceramic elements is kept as small as possible. This is advantageous, because stresses in the sensor which could be caused by different thermal exposure of individual portions are thereby avoided.

The ceramic elements are formed of a ceramic, e.g., of a ceramic material, using preferably the same ceramic for all elements. In its unsintered or green state, this ceramic can be provided with a structure. The use of a single ceramic is advantageous because it allows the ceramic elements to be structured with the same method, so that the manufacturing cost can be significantly reduced.

For the measurement of the heat flow, the sensor comprises at least one thermocouple arrangement which is formed along the heat flow path. The thermocouple arrangement generates a thermo-electric signal through which the heat flow can be determined in the conventional manner.

In general, the heat flow is measured directly or indirectly through a temperature measurement. Depending on the arrangement, an absolute temperature or also a temperature difference can be measured by means of the at least one temperature-measuring element. A temperature-measuring element can for example include an electrical resistor or a measurement chain with at least two thermocouples.

At least two thermocouples that are located at a distance from each other can form a measurement chain which, with appropriate connector contacts, can in turn represent a part of a thermocouple arrangement. With a measurement chain, the temperature difference between the thermocouples that make up the measurement chain can be determined. If the measurement chain is a so-called cold-junction circuit with one thermocouple formed inside the sensor and one thermocouple formed outside of the sensor, the measurement chain can also be used to determine an absolute temperature.

At least one of the thermocouples that belong to the thermocouple arrangement is formed within or on a layer of the sensor.

The heat flow that propagates within or on a layer can be determined by at least one measurement chain. The thermocouples that form the measurement chain can be formed inside and/or on a layer or also within and/or on different layers.

The determination of the heat flow which propagates in two dimensions on or within a layer normally occurs through a plurality of measurement chains, which in most cases represent a part of the thermocouple arrangements and are arranged on and/or within a layer.

For the determination of a heat flow that propagates perpendicular to a layer, a thermocouple arrangement can be laid out which is comprised substantially of measurement chains that extend between two or more layers.

The sensor in an exemplary embodiment comprises several measurement chains which are comprised of thermocouples that are arranged on and/or within a layer and/or on and/or within different layers. This makes it possible to measure the heat flow propagation in three dimensions.

A thermocouple usually comprises two different electrically conductive materials that are in contact with each other. The thermocouples can be produced by depositing and/or injecting metal-containing thermo-pastes onto and/or into the ceramic elements. It is possible for example to apply at least two different thermo-pastes to the ceramic elements by screen printing, or recesses provided in individual ceramic elements can be filled with different thermo-pastes. Thermocouples of the known state of the art comprise materials such as gold, silver, copper, palladium and platinum, as well as alloys of these metals. The term "recess" in this context includes indentations on as well as passages through a ceramic element.

The sensor can have measurement chains which can extend in the horizontal and/or vertical direction relative to the measurement position, with one or more measurement chains—each including at least two thermocouples—being arranged, e.g., not only within and/or on a layer but also on and/or between two or more layers.

The arrangement of horizontal and/or vertical measurement chains makes it possible to observe the heat flow propagation in the horizontal as well as the vertical direction. The arrangement of the measurement chains is very flexible so that, depending on the design of the sensor, it is for example also possible to arrange measurement chains comprising thermocouples in the vertical walls of recesses that are formed in the sensor to receive the sample or the reference. Depending on the arrangement of the measurement chains, the heat flow propagation can be observed in two or three dimensions.

The combination of horizontal and vertical measurement chains further allows a true three-dimensional arrangement of the thermocouples and thus a three-dimensional observation of the heat flow patterns in the sensor. This is very advantageous, as the accuracy of a calorimetric measurement depends on the number and arrangement of the thermocouples in and/or on the sensor. It has been found that a substantially circular arrangement of the thermocouples around the measurement position is especially advantageous. The thermocouples can therefore be distributed on a sensor surface and/or in a layer near the sensor surface as well as in all spatial dimensions inside the sensor in order to capture, inasmuch as it is possible, all of the heat flows and temperature gradients that establish themselves between a sample or reference and the temperature control device.

In a further exemplary embodiment, the thermocouple arrangement comprises at least one thermocouple that is formed on a surface of the sensor after the sintering process. This thermocouple can be produced with the conventional thick-film or thin-film technology. It is likewise possible to produce one or more thick-film or thin-film coating layers on the sensor after the sintering. One or more measurement chains can be formed in these coating layers as a part of the thermocouple arrangement by which the heat flow propagating on the sensor surface can be captured.

The temperature-measuring element can also comprise an electrical resistor which can be formed within and/or on a layer, and/or after the sintering on a surface of the sensor. The temperature-sensing can occur exclusively by way of one or more electrical resistors, exclusively by measurement chains, as well as by way of a combination of electrical resistors and measurement chains. An electrical resistor designed with a large surface area can even be used as a heating resistor, so that a local heating device is arranged within or on the sensor.

Thermocouples, electrical circuits, resistors and/or heating resistors can be formed for example by means of screen-printing techniques on the ceramic elements before the sintering, or on a surface of the sensor after the sintering.

The sensor in a further exemplary embodiment includes at least one conduit for fluids, in particular for temperature control fluids. By way of this conduit, the sensor and/or the sample or reference that is in contact with the sensor can be tempered, i.e. heated or cooled. The temperature control fluids that are used can be liquids, gases or liquified gases. Depending on the temperature control fluid and its temperature, the sensor can be heated and/or cooled. The conduit can be designed in any shape desired. To ensure a uniform heat exchange between the temperature control fluid and the sensor, it is appropriate if the fluids are kept moving through the conduits, which can be accomplished with conventional devices such as for example a pump.

Due to the capability to provide the ceramic elements with a structure, it is possible to change the heat conductivity of at least one sensor area, so that this area has a higher or lower heat conductivity than the ceramic. Such sensor areas either have at least one recess and/or a filled recess or include ceramic elements which are imprinted with a material whose heat conductivity deviates from the ceramic.

The possibilities for structuring the individual ceramic elements depend on their dimensions and on the ceramic being used. It is advantageous if the ceramic elements contain an aluminum oxide.

Essentially, the sensor is created by sintering an arrangement of individual structured and/or unstructured ceramic elements together in one process. The size of the individual ceramic elements is adapted to the dimensions and the shape of the finished sensor. Depending on the structure given to individual ceramic elements, it is possible to produce thermoanalytical sensors with different properties and shapes.

The shape of the sensor can affect its sensitivity, reproducibility and dynamic behavior, since these properties are determined essentially by the spatial distribution of the heat flows in the sensor. The sensitivity of the sensor is influenced primarily by the thermal resistance of different areas in the sensor, i.e. by the topology and the material between the thermocouples as well as the arrangement of the temperature-measuring elements and/or the measurement chains in the sensor.

The production of a sensor according to the disclosure comprises different steps and follows mainly a so-called LTCC (Low Temperature Co-fired Ceramics) method.

The base material used for producing the ceramic elements is an unsintered or green ceramic material. Green ceramic materials of the kind that are also used for LTCC ceramics are commercially available and can be obtained either in the shape of rolls or in already precut foil sheets of different sizes from different manufacturers such as e.g. DuPont or Heraeus. The base material has a thickness of, e.g., about 50 to about 300 µm.

To produce the individual ceramic elements of a given size, or arrays of ceramic elements which, similar to a silicon wafer, contain a plurality of ceramic elements which are separated from each other at a later point in time, the ceramic material which comes in rolls or in already precut foil sheets is cut up into platelets, ceramic elements or ceramic element arrays for example by laser-cutting, sawing, die-punching, milling or ultrasound cutting.

The individual ceramic elements or, in an industrial production process, arrays of elements can subsequently be structured if desired. The structuring of the individual ceramic elements can be performed on individual ceramic elements as well as on an array. Such an array is split up into individual ceramic elements in a later step of the process, for example after laminating or sintering.

After the structuring, the ceramic elements are in general thoroughly cleaned.

The ceramic elements which will eventually form a sensor are stacked on top of each other in a prescribed sequence. The properties and the shape of the sensor are determined essentially by the order of sequence of the structured and unstructured ceramic elements.

The stack assembled in this manner is subjected to a laminating operation prior to the sintering, so that the ceramic elements adhere to each other already before the sintering and cannot shift their positions relative to each other. The laminating is performed under pressure or in vacuum at temperatures below about 100° C.

Subsequently, the stack is sintered once. The sintering temperatures are higher than the laminating temperature and are typically below about 900° C. Through the sintering, the ceramic elements which already adhere to each other are solidly bonded to each other and form a nearly monolithic unit.

The structuring of the ceramic elements can comprise one or more of the following steps: One or more recesses can be produced for example by die-punching, laser-cutting, cutting or drilling. These recesses can in some cases be filled out again with different materials, whereby at these locations in the ceramic element, or at a later time in a layer, the material composition can be changed at specific points and/or in specific areas. If materials with a thermal conductivity different from the ceramic are used for the filling of the recesses, the thermal conductivity of the sensor can be changed or adapted in points and/or in areas. Materials that can be used include for example metals such as gold, platinum, palladium, copper, silver, and alloys of these metals, which have a high or, respectively, good thermal conductivity, and/or gases such as for example air, which have a low or poor thermal conductivity.

Metals can be used for example in the form of metal-containing pastes whose properties are adapted to the ceramic being used. However, other organic, inorganic or metallic materials can also be used for filling the recesses.

Furthermore, ceramic elements that have been pre-structured in this way as well as unstructured ceramic elements can be imprinted or coated with different materials. It is also possible to coat or imprint a surface of the unfinished sensor with further coatings after laminating or sintering. It suggests itself to use for this purpose the screen-printing methods that are known in the field of thick-film and thin-film technology, or also the conventionally known sol-gel processes and to thereby produce different patterns. These coatings can include, among other possibilities, one or more further temperature-measuring elements and/or one or more measurement positions.

As a further possibility for structuring, it is possible to use ceramic elements of different sizes, whereby the exterior shape of the sensor can be changed or individually adapted.

The forming of recesses and the subsequent filling and/or the imprinting of the ceramic elements and/or the imprinting of the sintered sensor can also be used to form at least one measurement position on the sensor.

In many cases the ceramic materials being used have the property that they shrink in the sintering process. It is therefore practical to make the individual ceramic elements slightly larger than the intended size of the sensor. If the layers consist substantially of structured ceramic elements, it might also be possible that they will not shrink uniformly.

In order to meet prescribed tolerances in regard to size and shape in the production process, it may be necessary to finish the sensor mechanically. The mechanical finish can for example include the splitting up of a stack of ceramic element arrays, a smoothing of the edges of the sensor and/or also a shaping of the final form of the sensor through methods such as cutting, grinding, drilling and/or milling. The size and shape of the sensor can further have an influence on the sensitivity and the measuring accuracy of the sensor.

After the sintering, the sensor can be mechanically finished and the at least one temperature-measuring element that is formed in the sensor can be electrically connected to a measuring unit and possibly also to a controller unit.

The structures that are formed in and/or on the ceramic elements in the course of the production process and/or the structures put onto the sensor represent different elements in the finished sensor, such as for example at least one temperature-measuring element, a thermocouple arrangement, an electrical resistor, and electrical heating resistor, a thermocouple, a measurement chain, a conduit for fluids and/or a sensor area with a heat conductivity different from the ceramic material.

The properties and the shape of the sensor are determined essentially by the order of sequence of the equally or differently structured and/or unstructured ceramic elements. Larger hollow spaces inside the sensor can occur for example by stacking several ceramic elements on top of each other which have recesses and/or cutouts in the same place, in which case it may be necessary to fill larger cavities with a space holder during the laminating and sintering, to ensure that the shape of the recess or the hollow space stays preserved after the sintering.

It is even possible in this way to form one or more tubelike conduits in the sensor. As the individual ceramic elements are solidly bonded to each other in the sintering process, these conduits will have closed walls after the sintering and can be used to carry temperature control fluids. Temperature control fluids can be liquids, gases or liquified gases. Depending on the fluid and its temperature, this allows the sensor to be heated or cooled. The leak-tightness of the conduits can be further improved for example by a subsequent coating of the walls.

The conduit for the temperature control fluids can be configured in any desired shape, where the conduit can run in a spiral shape below the measurement position or in a substantially meander-like shape. The conduits have connectors from the sensor to the outside, through which the conduits can be supplied from the outside with the temperature control fluid. For heat to be delivered or absorbed uniformly by the fluid, it is necessary to keep the fluids moving through the conduits, which can be accomplished with conventional devices such as pumps.

Finally, the at least one temperature-measuring element and/or the thermocouple arrangement is provided with electrical contact terminals, so that the temperature at one location and/or at different locations within and/or on the sensor can be measured and the heat flow can be determined.

BRIEF DESCRIPTION OF THE DRAWINGS

Different embodiments of a thermoanalytical sensor are described in the following with references to the drawing figures, wherein.

DETAILED DESCRIPTION

Figure 1:
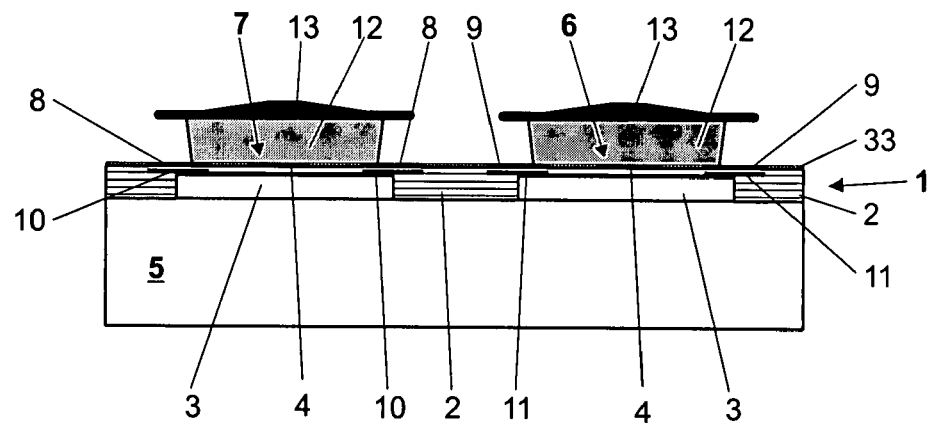
FIG. 1 represents a schematic cross-sectional view of a thermoanalytical sensor with several measurement chains, which is thermally coupled to a temperature control device and, by way of two measurement positions that are formed on the sensor, to a sample cup and a reference cup.
Figure 2:
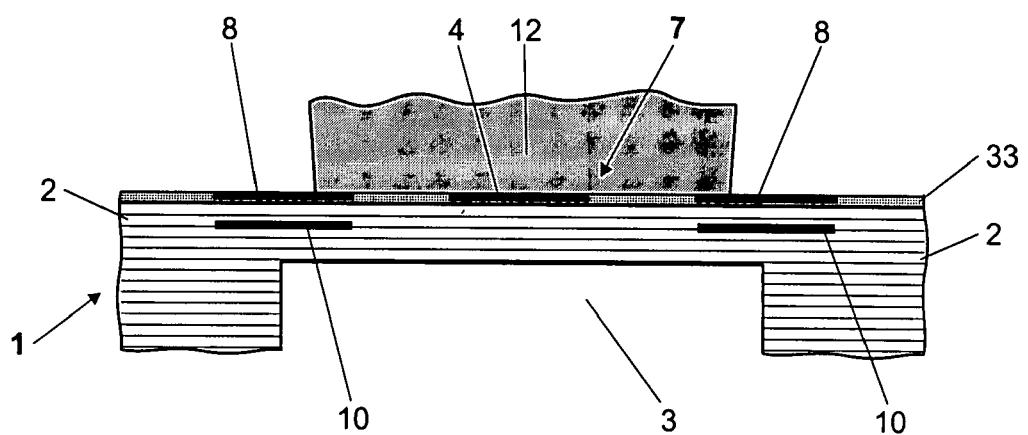
FIG. 2 shows an enlarged detail of FIG. 1.

FIGS. 1 and 2 illustrate an examplary embodiment of a thermoanalytical sensor for calorimetric measuring devices. Shown in FIG. 1 are the substantially disk-shaped sensor 1 which is comprised of a plurality of layers 2 that have been solidly bonded to each other by going through a sintering process together, and at least one coating layer 33 that has been applied to the sensor 1 after the sintering, together with a temperature control device 5 and one cup 12 each for a sample and a reference. For better clarity, FIG. 2 shows an enlarged detail portion of FIG. 1. FIGS. 1 and 2 will be explained together in more detail in the following.

For a better understanding of the structure of the sensor, the individual layers are shown in all of the drawing figures, although the layers can no longer be fully differentiated from each other after the sintering, but form a nearly monolithic unit in which the individual functional elements are formed.

The sensor 1 consists of several structured ceramic elements from which a sensor containing a plurality of layers 2 is created by putting the layered assembly through a joint sintering process at low temperatures. Subsequently, the sintered sensor in the illustrated example is coated with at least one further layer 33 which is applied for example in thick-film technology.

On the underside of the sensor 1 which is in contact with the temperature control device 5, two recesses 3 are formed by the structuring of individual ceramic layers before the sintering and/or after the sintering. These recesses are located below the measurement positions 6, 7 and reduce the thickness of the sensor in these areas. The recesses 3 enclose a vacuum or are filled with air or a gas. They are bordered by the temperature control device 5 which in this case is essentially a heater block consisting of silver.

The surface of the sensor that is in contact with the cups 12 is substantially a planar surface and is coated with at least one coating layer 33 which includes a structured part and an insulation part and is in this example applied by using thick-film technology. The structured coating part includes two measurement positions 6, 7 and, formed around each of the measurement positions 6, 7, a thermocouple arrangement which includes two of the measurement chains 8, 9 that are formed in the structured part of the coating layer 33. Each of the measurement chains 8, 9 has at least two thermocouples.

The sensor 1 illustrated in FIGS. 1 and 2 includes several measurement chains 8, 9, 10, 11. The measurement chains 8, 9 are formed in the coating layer 33, and the measurement chains 10, 11 are formed in and/or on a layer 2 lying inside the sensor. The measurement chains 8, 9, 10, 11 extend substantially in the radial direction around the measurement positions 6, 7. This allows temperature fluctuations to be detected not only in the radial direction around the individual measurement positions 6, 7 but also in different depths below the measurement positions 6, 7.

In addition there is a large-area electrical resistor 4 below each of the cups, which is in this example formed in the coating layer 33 and serves as a temperature-measuring element for determining an absolute temperature.

The sensor 1 includes several layers 2 which consist of a ceramic material that contains an aluminum oxide and is of the same type as used in the state-of-the-art LTCC processes. To form the measurement chains 10, 11, two thermocouples of two different thermo-pastes are formed on and/or in at least one layer. The measurement chains are located inside the sensor 1.

The measurement chains 10, 11 are formed already before the laminating through an appropriate structuring of individual ceramic elements. Together with the measurement chains 8, 9, they allow a three-dimensional measurement of the heat flow that moves between the substance under investigation and/or the reference and the temperature control device 5.

With the spatial separation, specifically the vertical distance, between the measurement chains 8, 9 and the measurement chains 10, 11, at least twice as many thermocouples can be formed in the sensor 1 in comparison to a conventional sensor, as the thermocouples are distributed on one or more layers 2 as well as in the coating layer 33 of the sensor. The sensitivity of the sensor is thereby increased in comparison to conventional sensors.

The two measurement positions 6, 7 that are formed after the sintering define the surface areas of the sensor on which the substance under investigation and/or the reference are arranged during a measurement. In general, the substance under investigation is put into a cup that can be closed with a cover 13, as shown in FIG. 1. For a reference, either an empty cup is used or a cup that is filled with a pure substance or a reference substance. Different kinds of cups are known, but for exact calorimetric measurements, the thermal, mechanical and chemical properties of the cups used have to be known. For calorimetric measurements, cups of a metal or a metal alloy are frequently used. Always, identical cups are used for the reference and the sample. Typical cup materials include among others aluminum, ceramics, steel, and sapphire.

LTCC ceramics are distinguished by the fact that they include a plurality of structured ceramic elements consisting in general of the same ceramic material, which are subjected together to a sintering process. Typical sintering temperatures are below about 900° C. Due to the relatively low sintering temperatures, the thermocouples can also be formed with thermo-pastes which contain metals with a low melting point such as gold, silver, copper, platinum, palladium and alloys of these metals, without the risk that the patterns and structures containing the thermo-pastes would lose their shapes.

Besides the measurement chains 10, 11, the recesses 3 are likewise produced by structuring the unsintered ceramic elements and are only mechanically finished after the sintering. The mechanical finish work may be required because the substrate material shrinks by a certain percentage of about 10% to 20% in the sintering process.

Already during the production process described above, different temperature-measuring elements such as thermocouples and/or electrical resistors can be formed on and/or inside of different ceramic elements. These thermocouples can form measurement chains that extend not only parallel to the surface of the sensor but also perpendicular to the latter, as shown in FIG. 3.

Figure 3:
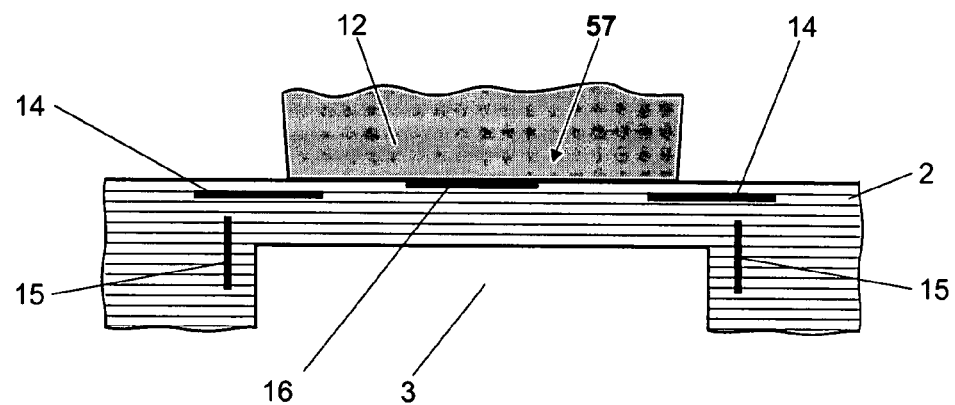
FIG. 3 provides a schematic enlarged representation of a thermoanalytical sensor with measurement chains arranged horizontally and vertically.

FIG. 3 represents an enlarged view of a part of a thermoanalytical sensor with vertical measurement chains 15, horizontal measurement chains 14, and a heating resistor 16 formed below the cup 12. The sensor itself is largely analogous to the sensor of FIGS. 1 and 2, with the same reference symbols being used for features that are identical.

The electrical heating resistor 16 is configured as a large-area resistor on a layer 2 and serves in this case as a local resistance-heating device for the sensor, so that the cup 12 can either be heated locally in addition to the temperature control device shown in FIG. 1 or exclusively through the resistor 16.

The sensor has vertical measurement chains 15 and horizontal measurement chains 14 which can be configured in a circular pattern around the measurement position that is located on the surface of the sensor. The vertical measurement chains 15 consist of at least two thermocouples which are formed inside and/or on two layers that have a vertical distance from each other.

The horizontal measurement chains 14 serve to detect a temperature difference between at least two thermocouples that are horizontally spaced apart from each other and are formed inside and/or on a layer 2.

The measurement chains consist of at least two thermocouples that are connected to each other, wherein each thermocouple includes at least two metallic materials with different conductivities. The individual thermocouples can be arranged in any desired two- or three-dimensional pattern around a measurement position.

The measurement chains 14, 15 which are arranged around a measurement position 57 and each of which has at least two thermocouples are combined into a thermocouple arrangement which can detect temperature fluctuations along the heat flow path that establishes itself between the measurement position 57 and the temperature control device (see FIG. 1). The combining of the measurement chains 14, 15 into a thermocouple arrangement takes place through suitable electrical connections between the thermocouples that form the measurement chains 14, 15, wherein the different thermocouples are normally connected in series. The contact terminals can be for conductor tracks printed on individual layers or on coatings deposited after the sintering (see FIGS. 1 and 2) as well as electrical conductors installed on the finished sensor.

The measurement chains arranged horizontally and vertically within and/or on a sensor allow a three-dimensional detection of the heat flows which during operation move between the sample or reference seated on the measurement position 57 and the temperature control device (see FIG. 1).

The thermocouples of the vertical measurement chain 15 as well as of the horizontal measurement chain 14 arranged in the sensor are produced already in the process of structuring the ceramic elements, or at least pre-formed and then produced in the subsequent sintering.

Figure 4:
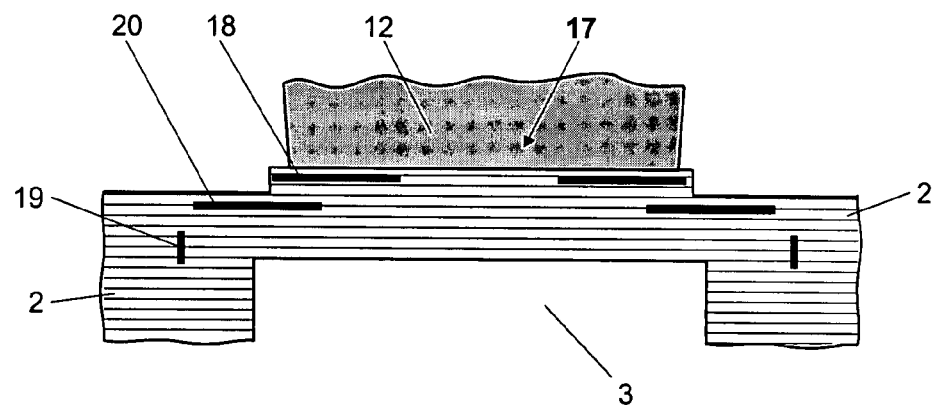
FIG. 4 provides a schematic enlarged representation of a thermoanalytical sensor with a raised seating area for a cup.

FIG. 4 shows a further possible configuration of a multi-layered sensor. The form of representation is substantially analogous to FIG. 3, and features that are identical are marked with the same reference symbols.

The thermoanalytical sensor in this embodiment has two horizontal measurement chains 18, 20 and a vertical measurement chain 19, all of which are arranged inside the sensor. Each of the measurement chains 18, 19, 20 has at least two thermocouples that are configured substantially in a circular pattern surrounding a measurement position 17. The measurement chains 18, 20 are arranged in layers that are distanced from each other in the vertical direction, and the orientation of the measurement chain 19 in the sensor is orthogonal to the measurement chains 18, 20.

The measurement position 17 is located on a raised seating area 21 which is likewise formed by a structuring of individual ceramic elements. The raised seating area 21 is formed through structuring several smaller ceramic elements. The complete sensor is subsequently laminated and sintered, so that a multi-layered sensor with the afore-described features is formed.

Figure 5:
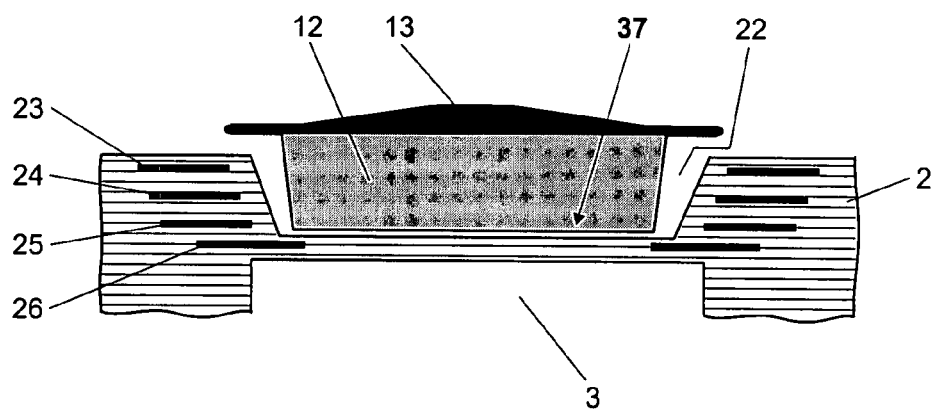
FIG. 5 provides a schematic enlarged representation of a thermoanalytical sensor with a sunken seating area for a cup.

FIG. 5 shows a sensor with a sunken seating area 22 serving to receive a closable sample- or reference cup 12. A measurement position 37 is formed on the floor of the sunken area 22, where a cup 12 can be placed which can be closed with a cover 13. The complete sensor consists of sintered ceramic layers 2 which contain several horizontal measurement chains 23, 24, 25, 26 which are spaced apart from each other in the vertical direction. The measurement chains 23, 24, 25, 26 are arranged on and/or inside of different layers 2, so that the cup 37 is surrounded laterally as well as from below by the measurement chains 23, 24, 25, 26.

The sunken area 22 can be produced either by die-punching or cutting of the respective areas from the unsintered ceramic elements, or by forming the recess 22 later in the sintered sensor, for example by milling or drilling. The sunken area or recess 22 can be formed prior to the sintering process, as a later machining operation could cause damage to individual thermocouples.

Figure 6:
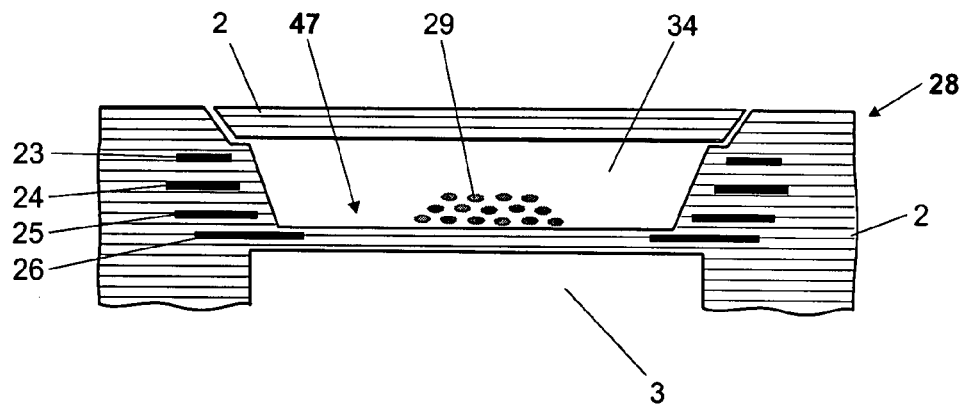
FIG. 6 provides a schematic enlarged representation of a thermoanalytical sensor with an integrally incorporated sample receptacle.

A further embodiment of the sensor is shown in FIG. 6. The sensor includes a receptacle for a sample or a reference, wherein the receptacle represents essentially a part of the sensor. A recess 34 is formed in the sensor which represents a cup serving to receive a sample or a reference. The recess 34 is covered and closed off by a lid 28 which likewise can include an LTCC ceramic comprised of several ceramic elements 2 that are sintered together. This creates a sample chamber 34 that can be closed off by the cover 28, where a sample 29 to be investigated can be placed directly into the sample chamber 34.

On the floor of the recess or sample chamber 34, there is again a measurement position 47 formed, which is surrounded by measurement chains 23, 24, 25, 26 that are arranged in several layers which are vertically distanced from each other. The thermocouples forming the measurement chains 23, 24, 25, 26 in this example are likewise produced by depositing and/or injecting different thermo-pastes on and/or into the unsintered ceramic elements, wherein the distances between at least two spatially separated thermocouples and thus the lengths of the measurement chains 23, 24, 25, 26 can differ from each other, as indicated in the drawing by the different lengths of the bars that symbolize the measurement chains 23, 24, 25, 26.

The thermal conductivity of multi-layered ceramic structures of the kind contained in the thermoanalytical sensors according to the disclosure can be influenced during the production process either by inserting a material of a better thermal conductivity than the ceramic into certain areas of the sensor or by creating recesses in the unsintered ceramic elements, which are then filled with a material of inferior thermal conductivity in comparison to the ceramic, for example air or vacuum.

Areas with a high thermal conductivity are created either by printing a pattern with a kind of thermally conductive paste onto individual ceramic elements or by making one or more recesses in the ceramic elements and filling them in a further step with a heat-conducting material.

Areas of reduced thermal conductivity are created by way of hollow spaces or recesses formed in these areas, which are filled with a material of poor thermal conductivity. The size of the hollow spaces is affected on the one hand by the size of the cutouts made in a ceramic element and on the other hand by overlaying a plurality of ceramic elements on each other whose cutouts are connected to each other.

Figure 7:
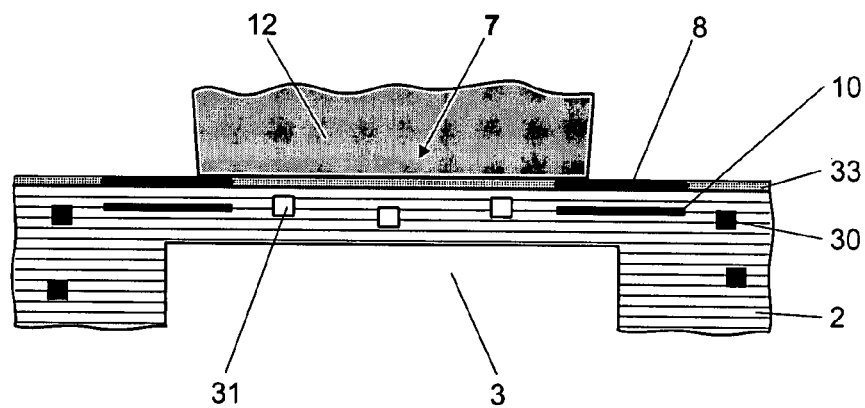
FIG. 7 provides a schematic enlarged representation of a thermoanalytical sensor which has domains with a thermal conductivity different from the ceramic material.

An example of a sensor which has domains with an adapted thermal conductivity is shown in FIG. 7. The illustration of the sensor is in part analogous to FIG. 2, and features that are identical have been marked with the same reference symbols. In a portion of the sensor that lies between the recess 3 and the measurement position 7, there are parts that contain a heat-insulating material 31 such as air or other thermal insulators. Due to the heat-insulating materials 31, the thermal conductivity in this area of the sensor is reduced, whereby the insulating effect of the recess 3 is further enhanced. As a result of the reduced thermal conductivity, these sensor portions are thermally insulated, whereby the amount of interaction between the thermocouple arrangements and the heat flow paths is reduced.

Sensor areas at the border or between two measurement positions should have a higher thermal conductivity in order to promote the heat transfer between the temperature control device and the measurement position 7. These areas are at least partially in direct contact with the temperature control device. An improvement of the thermal conductivity in these areas is achieved through cavities that are filled with a material 30 which has a higher thermal conductivity in comparison to the ceramic material, or by depositing the material 30 in prescribed, locally delimited patterns on individual ceramic elements.

Figure 8:
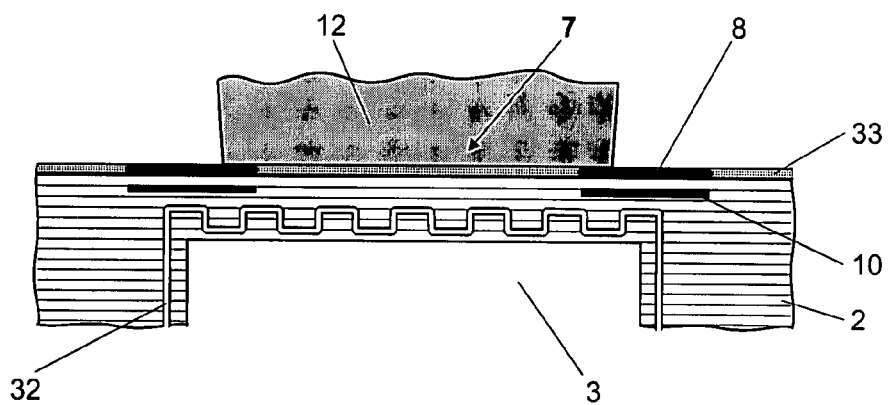
FIG. 8 provides a schematic enlarged representation of a thermoanalytical sensor with a conduit for temperature control fluids formed inside the sensor.

FIG. 8 shows a thermoanalytical sensor with a conduit 32 for temperature control fluids which is in this example meander-shaped. In the illustrated embodiment, the conduit 32 is arranged primarily below the measurement position 7, extending in an ideal case below the entire area that forms the measurement position. The conduit can for example also be spiral-shaped. The conduit 32 is comprised of interconnected hollow spaces which are formed in the unsintered ceramic elements. In the sintering process, the individual ceramic elements are permanently bonded to each other, so that a tubelike conduit 32 with solid, defined walls is produced through which the temperature control fluids can be conducted. The conduit 32 can be used for cooling as well as for heating the sensor and/or the cups placed on it. Depending on the area of application, temperature control liquids or gases such as for example water, air or liquid nitrogen are sent through the conduit 32. The fluids are moved for example by a conventional pump (not shown in the drawing) which is connected to the conduit 32. The conduit 32 is arranged in the sensor in such a way that it has at least one opening leading out of the sensor.

The embodiments presented here represent thermoanalytical sensors with different properties and features. To give a clearer overview, the different properties and features are shown in different embodiments, but it is also possible to implement individual features and properties as well as combinations of several or all of the disclosed features and properties in one sensor.

Depending on the configuration of the at least one sensor the thermoanalytical sensor according to the disclosure can be a sensor for calorimetric measurements that operates according to the power compensation principle or according to a differential method.

The embodiments presented here as examples include primarily thermoanalytical sensors with two measurement positions, i.e. a sample position and a reference position. However, it is also possible that the sensor has at least one reference position and more than one sample position, or that at least one sample and one reference are located on at least two sensors that are separate from each other and are only connected through at least one measuring unit and possibly in addition through a controller unit.

A sensor according to the disclosure includes at least one thermocouple arrangement that is formed in the sensor and can include at least one additional thermocouple arranged on the surface of the sensor.

All of the sensors in FIGS. 1 to 8 are shown in lengthwise sectional view. The illustrated structural features of the sensors such as for example the thermocouples, the conduit and the parts with reduced thermal conductivity can be either of a two-dimensional or three-dimensional configuration.

The measurement chains can be designed to surround the measurement positions according to any desired pattern, but the preference is for patterns which are circular or star-shaped in the widest sense of the word. If a sensor includes several thermocouples forming different measurement chains in different layers of the sensor, it suggests itself to put the thermocouples in the individual layers in staggered positions relative to each other, so that the heat flow can be captured overall in a larger area. It is also possible to form thermocouples and/or measurement chains not only within a layer but also over several layers.

A thermoanalytical sensor according to the disclosure is used primarily in calorimetric measurements, but it is also possible to determine the thermal conductivity of a substance and/or a material with a sensor of this kind.

Individual measurement chains always include at least two thermocouples which consist of different materials. The thermocouples are formed for example from thermo-pastes that contain gold, platinum, silver, palladium, copper, and alloys of these metals.

Instead of or in addition to the measurement chains, a temperature measurement and/or a determination of an absolute temperature can take place with temperature-measuring elements that measure the temperature by means of an electrical resistor. Electrical resistors can be formed in one layer or in several layers and/or in a coating deposited for example in thick-film technology after the sintering process.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

LIST OF REFERENCE SYMBOLS

1 sensor
2 layer
3 cutout, recess
4 electrical resistor
5 temperature control device
6 measurement position
7 measurement position
8 measurement chain
9 measurement chain
10 measurement chain
11 measurement chain
12 cup
13 cover, lid
14 horizontal measurement chain
15 vertical measurement chain
16 electrical resistor
17 measurement position
18 horizontal measurement chain
19 horizontal measurement chain
20 vertical measurement chain
21 raised seating area
22 recess, sunken area
23 horizontal measurement chain
24 horizontal measurement chain
25 horizontal measurement chain
26 horizontal measurement chain
27 measurement position
28 cover, lid
29 substance
30 heat-conducted material
31 heat-insulated area, hollow space
32 conduit
33 coating
34 recess, sample chamber
37 measurement position
47 measurement position
57 measurement position

What is claimed is:

1. A thermoanalytical sensor for calorimetric measurements comprising:
   at least one measurement position formed on the sensor for establishing, when used with a temperature control device, heat flow paths between the measurement position and the temperature control device, said heat flow paths propagating in three-dimensions through said sensor; and
   at least one thermocouple arrangement that is formed along a plurality of said heat flow paths for generating a thermoelectric signal, wherein the at least one thermocouple arrangement comprises at least one temperature-measuring element,
   wherein:
   the sensor is comprised of a plurality of layers which are formed substantially by jointly-sintered ceramic elements that have been solidly bonded to each other by undergoing a single joint sintering process,
   at least a part of the ceramic elements have been structured in their green state prior to sintering, and
   the thermocouple arrangement measures heat flow propagation in said three-dimensions.

2. The thermoanalytical sensor according to claim 1, wherein the temperature-measuring element comprises at least one measurement chain which is comprised of at least two thermocouples and is part of the at least one thermocouple arrangement.

3. The thermoanalytical sensor according to claim 2, wherein the at least one thermocouple arrangement comprises at least one thermocouple formed within or on a layer.

4. The thermoanalytical sensor according to claim 2, comprising at least two thermocouples which are formed within and/or on one layer.

5. The thermoanalytical sensor according to claim 2, wherein said at least two thermocouples are formed within and/or on different layers.

6. The thermoanalytical sensor according to claim 1, wherein the temperature-measuring element comprises at least one electrical resistor.

7. The thermoanalytical sensor according to claim 1, comprising at least one electrical heating resistor formed in the sensor.

8. The thermoanalytical sensor according to claim 1, wherein at least one conduit for fluids is formed in the sensor.

9. The thermoanalytical sensor according to claim 1, wherein said thermoanalytical sensor comprises at least one sensor portion with a thermal conductivity that differs from the thermal conductivity of unstructured ceramic elements.

10. The thermoanalytical sensor according to claim 9, wherein said sensor portion with a given thermal conductivity comprises at least one hollowed-out space and/or at least one back-filled hollow space.

11. The thermoanalytical sensor according to claim 1, wherein the ceramic elements comprise aluminum oxide.

12. The thermoanalytical sensor according to claim 1, wherein the ceramic elements comprise one or more of the following:
at least one hollow space and/or
at least one filled hollow space.

13. The thermoanalytical sensor according to claim 1, wherein one or more of the following elements are formed within and/or on the sensor: a temperature-measuring element, an electrical resistor, a thermocouple, a measurement chain, a thermocouple arrangement, a conduit for fluids, an electrical heating resistor and a sensor portion with a thermal conductivity which deviates from the thermal conductivity of the ceramic material.

14. The thermoanalytical sensor according to claim 1, wherein at least one thermocouple in the at least one thermocouple arrangement is disposed on a surface area of the sensor.

15. The thermoanalytical sensor according to claim 1, wherein the at least one temperature-measuring element and/or the at least one thermocouple arrangement are provided with contact terminals and connected to a controller unit.

16. The thermoanalytical sensor according to claim 1, in combination with a temperature control device.

* * * * *